US012626014B2

(12) United States Patent
Santhanam et al.

(10) Patent No.: US 12,626,014 B2
(45) Date of Patent: May 12, 2026

(54) DYNAMIC ACCESS CONTROL TO ELECTRONIC PATIENT RECORDS

(71) Applicant: Helix, Inc., San Mateo, CA (US)

(72) Inventors: Sharad Santhanam, Sunnyvale, CA (US); Anna Swigart, Seattle, WA (US); Geraint Levan, San Marcos, CA (US)

(73) Assignee: Helix, Inc., San Mateo, CA (US)

( * ) Notice: Subject to any disclaimer, the term of this patent is extended or adjusted under 35 U.S.C. 154(b) by 142 days.

(21) Appl. No.: 18/762,260

(22) Filed: Jul. 2, 2024

(65) Prior Publication Data

US 2026/0010648 A1     Jan. 8, 2026

(51) Int. Cl.
| | |
|---|---|
| *G06F 21/62* | (2013.01) |
| *G16H 10/60* | (2018.01) |
| *G16H 50/20* | (2018.01) |
| *H04L 9/32* | (2006.01) |

(52) U.S. Cl.
CPC ......... *G06F 21/6245* (2013.01); *G16H 10/60* (2018.01); *G16H 50/20* (2018.01); *H04L 9/3236* (2013.01); *G06F 2221/2141* (2013.01)

(58) Field of Classification Search
CPC .... G06F 21/6245; G16H 10/60; G16H 50/20; H04L 9/3236
See application file for complete search history.

(56) References Cited

U.S. PATENT DOCUMENTS

| | | | |
|---|---|---|---|
| 2015/0223057 A1* | 8/2015 | Dellarciprete ...... | G06F 21/6245 |
| | | | 455/410 |
| 2017/0091391 A1* | 3/2017 | LePendu ............. | G06F 21/6245 |
| 2018/0137247 A1* | 5/2018 | Bore ...................... | G16H 80/00 |
| 2024/0177843 A1* | 5/2024 | Alsubai ................. | G06Q 40/08 |

OTHER PUBLICATIONS

Wilnellys Moore et al., Review of HIPAA, Part 1: History, Protected Health Information, and Privacy and Security Rules, The society of Nuclear Medicine and Molecular Imaging (Year: 2019).*
Cyera Website accessed Jul. 11, 2024 https://www.cyera.io/platform.
Immuta Website "De-risk your data" accessed Jul. 11, 2024 www.immuta.com/.
NIST Website "Attribute Based Access Control ABAC" accessed Jul. 11, 2024 https://csrc.nist.gov/projects/attribute-based-access-control.

* cited by examiner

*Primary Examiner* — Shanto Abedin
(74) *Attorney, Agent, or Firm* — FisherBroyles, LLP; Gregory T. Fettig

(57) ABSTRACT

Systems and methods herein provide for access control to information in electronic patient records. One method includes receiving a request from an entity for access to one or more of a plurality of electronic patient records, the records having been machine learned to identify patient information in the electronic patient records including personally identifiable information and protected health information. The method also includes determining a level of access of the entity, retrieving, from a database, the one or more electronic patient records requested by the entity, applying a rule to the retrieved one or more electronic patient records based on the determined level of access of the entity to mask, encrypt, show, etc. one or more elements in the one or more electronic patient records. In response to applying the rule to the retrieved one or more electronic patient records, the electronic patient records are transferred to the entity.

18 Claims, 6 Drawing Sheets

300

304-1 – 304-N

Data Classifier
308

Entity/Role Management I/F
322

306-1 – 306-N

Machine Learning Module
330

Metadata Repository
310

320-1 – 320-N

Database
302

316

Policy Executor
318

Rules Engine
314

Entity Locator
312

324

400

410A

| Customer Name | Market Segment | Phone Number | Account Balance | Income |
|---|---|---|---|---|
| John Smith | Household | 720-555-1234 | $1234.32 | middle |
| Jane Doe | Machinery | 719-555-4567 | $6532.41 | high |
| Robert Jenkins | Building | 820-555-3456 | $514.67 | low |
| Susan Homemaker | Household | 831-555-2345 | $2964.49 | middle |
| | | | | |
| | | | | |
| | | | | |

| Customer Name | Market Segment | Phone Number | Account Balance | Income |
|---|---|---|---|---|
| XXXXXXXX | NULL | 38373005079... | $1234.32 | middle |
| XXXXXXXX | NULL | 68473766378 1... | $6532.41 | high |
| XXXXXXXX | NULL | 34827054327 8... | $514.67 | low |
| XXXXXXXX | NULL | 33579956431 7... | $2964.49 | middle |
| | | | | |
| | | | | |
| | | | | |

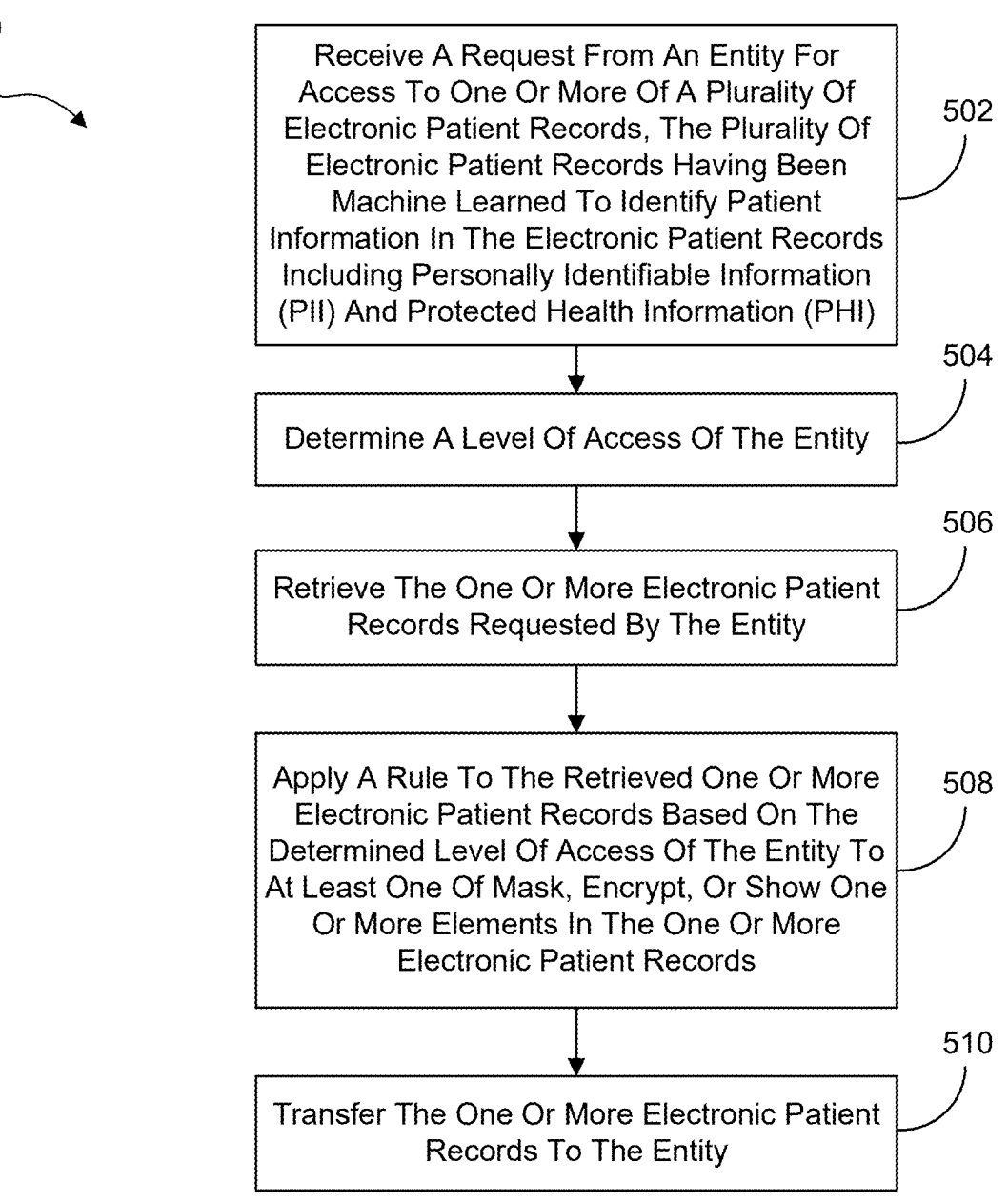

500

Receive A Request From An Entity For Access To One Or More Of A Plurality Of Electronic Patient Records, The Plurality Of Electronic Patient Records Having Been Machine Learned To Identify Patient Information In The Electronic Patient Records Including Personally Identifiable Information (PII) And Protected Health Information (PHI) — 502

Determine A Level Of Access Of The Entity — 504

Retrieve The One Or More Electronic Patient Records Requested By The Entity — 506

Apply A Rule To The Retrieved One Or More Electronic Patient Records Based On The Determined Level Of Access Of The Entity To At Least One Of Mask, Encrypt, Or Show One Or More Elements In The One Or More Electronic Patient Records — 508

Transfer The One Or More Electronic Patient Records To The Entity — 510

DYNAMIC ACCESS CONTROL TO ELECTRONIC PATIENT RECORDS

FIELD

The disclosure relates to the field of access control on information in electronic patient records.

BACKGROUND

Healthcare providers and researchers maintain many data tables and data stores (e.g., thousands or more) on a daily basis. Many of these data tables include personally identifiable information (PII) and protected health information (PHI). Existing techniques for deciding whether data from these sources can be shared and/or the extent to which that data can be shared generally involves manual review by a specialist. For example, if data within a portion of a table has PII or PHI, the specialist marks the data as such, and generates a new version of the table that omits the PII or PHI. In many cases, the specialist may create two versions of the data table—one in which the PII and/or PHI has been omitted, and another in which it has not. A data table that has not been culled for PII or PHI may then be distributed to a small cadre of persons having sufficient access rights to review it, while the revised data table may be distributed to a separate group of persons with limited or no access rights.

These existing procedures encounter numerous problems. For example, the sheer amount of data that is reviewed by the specialist is daunting, and many tables are never even reviewed for the possibility of sharing with others. Instead, they are simply restricted from view by others, as the specialist has no time to review them. Additionally, the data tables are often updated regularly with new columns of data, triggering the need for supplemental review by a specialist whenever this occurs.

This process is subject to human error on multiple fronts. For example, a specialist may mis-mark a type of data, resulting in under sharing or over sharing of information. The specialist may also provide unredacted tables to the wrong persons. This may result in potential leakage of PII or PHI. The specialist may also fail to identify or review a change to a data table before that data table is shared with others, again resulting in potential leakage of PII or PHI. Thus, there exists a need to automate data access processes to ensure that information and electronic patient records is protected.

SUMMARY

Embodiments described herein advantageously combine automated data classification with dynamic database policies that are attached to individual data tables and maintained as stored procedures within a database. As new queries to the database are supplied, the queries are reviewed, and content is selectively supplied to an entity making the query based on the role of the entity, the classifications of data within the table, and the stored procedures within the table for the entities.

In some embodiments, the database supplies masked (e.g., hashed) versions of data when an entity does not have permission to access the underlying data. This may permit certain operations (e.g., mathematical operations, counts, etc.) that rely on the underlying data to be performed without revealing the underlying data itself.

In one embodiment, a computer implemented method includes receiving a request from an entity for access to one or more of a plurality of electronic patient records. The plurality of electronic patient records has been machine learned to identify patient information in the electronic patient records including personally identifiable information (PII) and protected health information (PHI). The computer implemented method also includes determining a level of access of the entity, retrieving, from a database, the one or more electronic patient records requested by the entity, applying a rule to the retrieved one or more electronic patient records based on the determined level of access of the entity to at least one of mask, encrypt, or show one or more elements in the one or more electronic patient records, and, in response to applying the rule to the retrieved one or more electronic patient records, transferring the one or more electronic patient records to the entity.

In some embodiments, encrypting the one or more elements in the one or more electronic patient records includes applying a hash encryption to the one or more elements in the one or more electronic patient records. In some embodiments, the computer implemented method also includes receiving a new electronic patient record, and machine learning the new electronic patient record with a machine learning model that has been trained on the plurality of electronic patient records. In this regard, the computer implemented method may also include restricting access to all elements of the new electronic patient record until all elements of the new electronic patient record have been identified.

In some embodiments, the computer implemented method includes receiving a new element to at least one of the plurality of electronic patient records, and restricting access to the new element of the at least one electronic patient record until the new element of the at least one electronic patient record has been identified. The computer implemented method may also include determining a level of access of the entity further comprises identifying an entity role for the entity when the entity logs into the database. The level of access of the entity may include one of access to public data, access to confidential data, access to data having indirect identifiers for PII and/or PHI, access to data having direct identifiers for PII and/or PHI, access to genetic data, and access to restricted data.

Other illustrative embodiments (e.g., systems and computer-readable media relating to the foregoing embodiments) may be described below. The features, functions, and advantages that have been discussed can be achieved independently in various embodiments or may be combined in yet other embodiments, further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 4A illustrates various electronic patient records, in an illustrative embodiment.

FIG. 4B illustrates the electronic patient records of FIG. 4A with various forms of access control being implemented, in an illustrative embodiment.

FIG. 5 is a flowchart of a method for providing access control to electronic patient records, in an illustrative embodiment.

DESCRIPTION

The figures and the following description depict specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
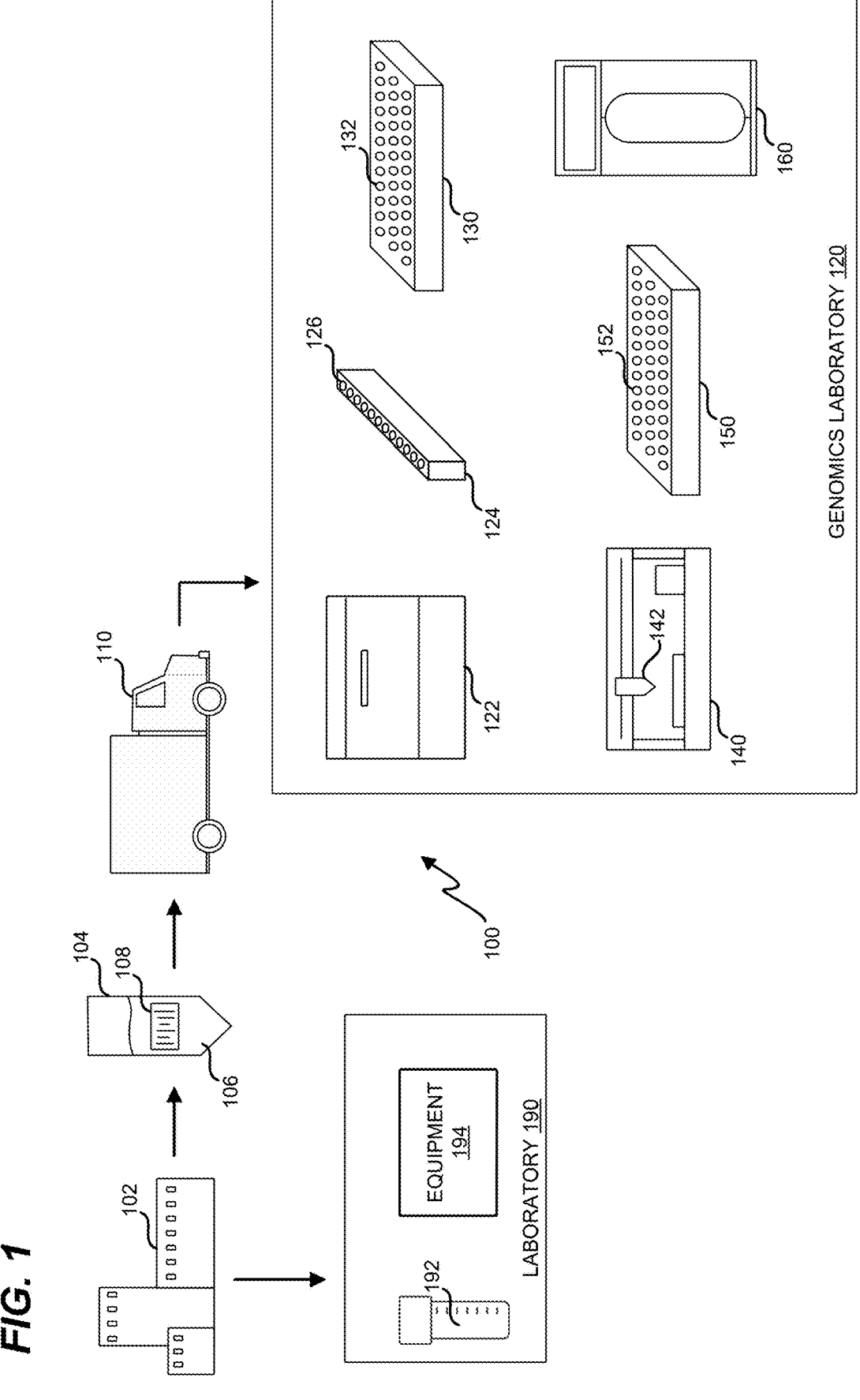
FIG. 1 is a diagram depicting a sample processing architecture, in an illustrative embodiment.

FIG. 1 is a diagram depicting a sample processing architecture 100 in an illustrative embodiment. Sample processing architecture 100 comprises any system or organizational structure for acquiring and sequencing biological samples in a high-volume, high-throughput manner. Sample processing architecture 100 may be utilized, for example, to collect and sequence genetic material (in the form of Ribonucleic Acid (RNA) or Deoxyribonucleic Acid (DNA)) found within thousands or tens of thousands of samples 106 daily, via multiple healthcare providers 102.

Healthcare provider 102 may comprise hospitals, clinics, practitioner offices, laboratories, surgical centers, etc. that engage in or facilitate the practice of medicine. In one embodiment, healthcare providers 102 comprise groups of hospitals that treat millions of patients. As a part of the practice of medicine, healthcare provider 102 acquires samples 106 for sequencing. For example, a healthcare provider 102 may acquire samples 106 as part of a population screening program, as part of medical treatment, etc. The specific amount of sequencing desired for a sample 106 may comprise a selected set of one or more genes, an exome, the entire genome of a patient, etc. The samples 106 are stored in sample containers 104, which may be accompanied by Customer Sample Identifiers (CSIs) 108. A delivery service 110 provides the samples 106 to a genomics laboratory 120 for processing.

Healthcare provider 102 may also acquire samples 192 for blood testing. These samples 192 may be provided to laboratory 190 for analysis via equipment 194 (e.g., a chemically treated test strip, biochemical assay, etc.), or may be analyzed by patients via at-home testing methods. Sample processing architecture 100 provides a technical benefit by allowing laboratory 190 and genomics laboratory 120 to specialize in different methods of analysis.

Procedures within genomics laboratory 120 related to genetics may include accessioning, sample plating, storage, extraction, library preparation, enrichment, and sequencing processes. These processes acquire genetic material from a sample 106, separate the genetic material from other constituents, duplicate the genetic material, and quantify the genetic material order to determine a swathe of sequence data, such as an exome or entire genome for a subject (e.g., a human patient, an organelle of a human patient, etc.).

Although the procedures discussed herein are specific with regard to one method of sequencing, other techniques may be utilized in accordance with known standards in order to perform sequencing for samples 106. For example, although some of the techniques discussed herein relate to hybridization capture techniques, amplicon-based techniques may be used.

Accessioning

Accessioning refers to receiving and preparing samples 106 for later laboratory processes. In one embodiment, accessioning includes receiving a batch of samples 106 (e.g., hundreds or thousands of samples 106) from one or more delivery services 110 each day for processing. For example, packages that each include tens or hundreds of samples 106 may be delivered to genomics laboratory 120 via the United States Postal Service (USPS), or a private package carrier.

Each sample 106 may be retained within a sample container 104, such as a five milliliter (mL) test tube. In this embodiment, the sample container 104 is sealed to prevent the sample 106 from being exposed to the environment and also to prevent the sample 106 from co-mingling with other samples 106. For example, the sample 106 may be sealed via a cap that is threaded, glued, press-fit, etc. At the time of delivery, the sample container 104 may further include a remnant of a sampling tool, such as a portion of a swab that was utilized to acquire the sample.

In many embodiments, a CSI 108 for the sample 106 is reported via a component affixed to or integrated with the sample container 104. The CSI 108 uniquely distinguishes the sample 106 from other samples 106 being received. For example, a CSI 108 may uniquely distinguish a sample 106 from other samples 106 in the same batch, other samples 106 received on the same date, other samples 106 received from the same healthcare provider 102, etc. A CSI 108 may be reported via a barcode label, Quick Response (QR) code label, Radio Frequency Identifier (RFID) chip, or any suitable visual, transmission-generating, or other physical component affixed to or integrated with the sample container 104.

In further embodiments, the sample container 104 is itself sealed within an external container such as a bag (not shown). Using an external container helps to prevent contamination, by ensuring that a technician at the genomics laboratory 120 does not contact biological material from the sample 106 that may exist on an outer surface of the sample container 104. Use of an external container may also be required by law (e.g., Department of Transportation (DOT) guidelines). Use of an external container additionally helps to prevent cross-contamination between samples 106. Furthermore, in embodiments where samples 106 may include blood or a pathogen, an external container provides an additional barrier to protect the health of technicians. The external container may additionally include documentation confirming the CSI 108, information for the subject that the sample was sourced from, and/or information indicating circumstances of sampling. The circumstances of sampling may include, for example, a sampling date, a sampling method, a location that the sample was acquired, a name or title for a person who performed the sampling, and/or additional notes.

In this embodiment, the sample 106 comprises a chemical solution. For example, the sample 106 may comprise a prepared aqueous solution such as a saline solution, or may comprise a bodily fluid such as blood, saliva, mucus, etc. In some embodiments each of the samples 106 fills between two and five milliliters of volume within its corresponding sample container 104.

The samples 106 further include genetic material such as Deoxyribonucleic Acid (DNA), Ribonucleic Acid (RNA), etc. In many instances, the genetic material is one of many constituent components within the sample 106. For example, the genetic material may exist within the nuclei of white blood cells that are included within the sample 106. In a further example, genetic material may exist within viruses or bacteria within the sample 106. In this embodiment, the genetic material is not yet isolated from the remaining constituent components of the sample 106.

After receipt of the samples 106, batches of the samples 106 (e.g., as stored within sample containers 104 and/or external containers) may be heated in ovens 122 to facilitate cell lysis. The temperature, and duration of heating, may be chosen such that pathogenic material within the samples 106 is rendered harmless, or such that cellular lysis occurs. For example, heating may occur at a temperature of between forty and eighty (e.g., fifty) degrees Celsius (C), for a period of time between fifteen and two hundred (e.g., thirty) minutes. In some embodiments, including embodiments wherein the samples 106 are primarily the contents of a blood draw, the heating step may be foregone.

Upon completion of heating, the batches of samples 106 are removed from the ovens 122. In one embodiment, sample containers 104 are removed from corresponding external containers, such as by cutting the external containers open. With the sample containers 104 now available for direct interaction, the sample containers 104 are inspected. As a part of this process, a technician or automated system may determine the CSI 108 for the sample 106, and may compare the CSI 108 to a CSI 108 listed on documentation provided in the external container. If there is a discrepancy between the CSI 108 on the sample container 104 and a CSI 108 listed in the documentation, the sample 106 may be flagged as having an error condition. Similarly, if the CSI 108 on the sample container 104 is damaged (e.g., abraded, heat-damaged, or water-damaged) and has become unreadable, the sample 106 may be flagged as having an error condition.

A technician or automated system may further inspect the contents of the sample container 104, via visual or other methods. If the sample 106 does not include an expected constituent component (or is otherwise non-compliant) then the sample 106 is flagged as having an error condition. For example, if the sample 106 is primarily saliva and includes a fluid that is not permitted (e.g., blood), includes an entire swab or no swab, appears to have a fractured or broken casing, or is outside of an expected range of volume (e.g., between two and five milliliters), then the sample 106 may be flagged as having an error condition.

Samples 106 that have not been flagged as having an error condition proceed to sample integration. In one embodiment, as a part of sample integration, the sample 106 is assigned a Laboratory Sample Identifier (LSI). The LSI uniquely identifies the sample 106 from other samples 106 received for the batch, received on the same day, processed in the same laboratory, and/or handled by the same organization performing sequencing. In many embodiments, the LSI is stored in a memory of a genomics server (e.g., within a laboratory sample database), and is uniquely associated with a corresponding CSI 108 for the sample. The LSI may also be associated with any error conditions reported for the sample 106.

In many embodiments, CSIs 108 originally provided with the samples 106 are in the form of a paper barcode. In such embodiments, the paper barcode may be printed in aqueous ink. This renders the barcode subject to degradation upon exposure to liquid in the laboratory environment, which is undesirable.

To ensure that each sample container 104 is capable of traveling through the genomics laboratory 120 without its identifier being physically degraded, a corresponding LSI may be indicated at the sample container 104. The LSI may be indicated via the application of a barcode label, Quick Response (QR) code, Radio Frequency Identifier (RFID) chip, or other visual, transmission-generating, or other physical component affixed to or integrated with the sample container.

In one embodiment, the LSI is printed onto a barcode label comprising rip-proof material (e.g., vinyl) in a water-insoluble ink. This implementation ensures that the barcode label is resistant to physical and chemical degradation. The barcode may be applied around an entire perimeter of the sample container 104, ensuring that the sample container 104 may be scanned from any angle.

In further embodiments, the element used to report the LSI is accompanied by a visually distinct mark that enables rapid confirmation by a technician that the sample 106 has been integrated into the laboratory environment. The visually distinct mark may comprise a colored ring (e.g., around an entire perimeter of the sample container), a logo, a physical feature, a stamp, etc.

Sample Plating

With the samples 106 having been successfully integrated into the environment of the genomics laboratory 120 environment, the samples 106 are ready for analytics to be performed. To this end, the samples 106 are prepared for transfer to a sample microplate 130. The sample microplate 130 may be labeled with a unique identifier via similar techniques to those used for sample containers 104 above. The unique identifier distinguishes the sample microplate 130 from other sample microplates 130. In one embodiment, the sample microplate 130 comprises a solid body defining three hundred and eighty-four wells, distributed across sixteen rows and twenty-four columns, each well having a capacity of between thirty and one hundred microliters. In a further embodiment, the sample microplate 130 comprises a solid body defining ninety-six wells, distributed across eight rows and twelve columns, each well having a capacity of between one hundred and three hundred microliters. Any suitable number and arrangement of wells may be selected as a matter of design choice.

As a part of preparing the samples 106 for transfer to the sample microplate 130, a technician may place sample containers 104 onto a rack 124, and scan each sample container 104 to determine an LSI for each location 126 (e.g., each container receptacle) on the rack 124. In some embodiments, the rack 124 is assigned a unique identifier that distinguishes it from other racks 124. The rack 124 may be labeled with a unique identifier using techniques similar to those used for sample containers 104. The technician, or automated machinery such as a server operating an optical scanner, may then associate the unique identifier for the rack 124, along with the locations 126 assigned to the samples 106, with the corresponding LSIs of the samples 106 stored at the rack 124.

The technician additionally unseals the sample containers 104. Unsealing of sample containers 104 may be a deeply labor-intensive process, particularly when laboratory processes are performed at scale to handle tens of thousands of samples 106 per day. Thus, a technician may utilize automated tooling to enhance the speed at which sample containers 104 are unsealed. The tooling may, for example, unscrew, cut, or drill each sample container 104, in order to make the sample 106 within available for physical transfer to the sample microplate 130.

One or more racks 124 of samples 106 are provided to a Liquid Handler (LH) 140, such as an automated robot that operates an end effector 142 in accordance with one or more Numerical Control (NC) programs to transfer liquids between wells via arrays of micropipettes. An LH 140 is also known as a "Liquid Handling System." LH 140 may comprise, for example, a Hamilton Microlab Star Liquid Handling System.

In this embodiment, the LH 140 proceeds to transfer a portion of each sample 106 at a rack 124 to a well 132 within the sample microplate 130 that is not shared with other samples 106. For example, the well 132 for each sample 106 may be predetermined in accordance with a control program used by the genomics laboratory 120. In one embodiment, the LH 140 transfers the portions of the samples 106 to the wells 132 of the sample microplate 130 by providing instructions to actuators, piezoelectric elements, and/or pressure systems operating the end effector 142. In such an embodiment, the end effector 142 may align its array of micropipettes with the sample containers 104 to retrieve portions of the samples 106. Furthermore, in such an embodiment, the end effector 142 may dynamically align its array of micropipettes with the sample microplate 130 to deposit the portions of the samples 106 at the wells 132.

Because there is a known relationship between locations 126 at the rack 124 and wells 132 of the sample microplate 130 (e.g., as indicated by row and column), contents of the memory of a genomics server (e.g., a laboratory sample database) may be updated to indicate the well 132 storing genetic material for each sample 106. In one embodiment, the memory is further updated to associate a unique identifier for the sample microplate 130 with the samples 106 stored therein.

In one embodiment, programmed instructions for the LH 140 may direct the end effector 142 to position itself above a set of disposable tips, descend into the tips to attach the tips, reposition the end effector 142 above the rack of sample containers 104, adjust spacing between micropipettes within the array, descend until the tips reach the sample containers 104, draw liquid from the sample containers 104, deposit the liquid into a well at the sample microplate 130, and then dispose of the tips. Such a process may be repeated across sample containers 104 stored on multiple racks until the sample microplate 130 is filled with portions from the samples 106. In one embodiment, one or more wells 132 on the sample microplate 130 are filled with a control reagent instead of a portion of a sample 106.

The amount of liquid drawn from each sample container 104 may comprise a small fraction of the overall volume of the sample container 104. For example, an amount of liquid drawn may comprise several microliters, such as between two and ten microliters. Upon completion of transfer from the sample containers 104 to the wells, the sample microplate 130 may be covered with a liquid and/or gas-impermeable layer, such as foil or paraffin. Sample containers 104 remaining on the racks may be resealed, for example with pressure-fit caps having a color distinct from an original color for the sample containers. With accessioning now complete for the sample microplate 130, the sample microplate 130 is transferred to a next section of the laboratory for processing.

Storage

In one embodiment, accessioned samples 106, samples 106 ready for analytics, and/or samples 106 that have already been sequenced, are stored for later use. For example, samples 106, sample containers 104, and/or sample microplates 130 may be stored at room temperature, or may be cryogenically frozen at a low temperature (e.g., negative eighty degrees Celsius) and arranged in racks for later retrieval. Samples 106 may be preserved for periods of days or years, enabling rapid re-testing to be performed for subjects without the need for re-acquiring genetic material. Storage of the samples 106 provides notable value in the event that contents of a well 132 used for sequencing do not meet with rigorous quality control standards. Specifically, storage enables re-sampling to occur in the event that there is a desire to resequence a sample 106.

Extraction

Sample microplates 130 are transferred to a portion of the genomics laboratory 120 dedicated to extraction of the genetic material. The segment of the laboratory 120 that performs extraction and other pre-amplification operations may be sealed from, and/or positively pressurized relative to, other portions of the genomics laboratory 120.

During extraction, a sample microplate 130 is acquired and provided to an LH 140. The LH 140 that performs extraction may be different from the LH 140 that performs sample plating. The LH 140 may apply a reagent to each well 132 that lyses cells within each well. For example, this may be performed in order to lyse white blood cells containing genetic material for a human, or may comprise lysing other types of cells to expose other types of genetic material. The reagents used for pre-amplification processes may be stored at the LH 140 in a temperature-controlled manner, and may even be vibrated or mixed on a regular basis to ensure that the reagents are evenly distributed in suspension.

In one embodiment, extraction further includes an LH 140 aspirating and dispensing reagents that selectively bind to genetic material released from the lysed cells. This process may include applying a bead (not shown) to the well 132. In one embodiment, the beads comprise magnetic beads that selectively bind to the genetic material (e.g., DNA). This allows for isolation and purification of the genetic material while contaminants remain in solution. In one embodiment, the magnetic bead is drawn to a magnetic base at or under the sample microplate 130. After the genetic material has been drawn to the bead, and after the bead has been secured to the base of the well, a flushing step may be performed wherein remaining fluid in each well is washed away. This ensures that potential impurities are removed from the well. The LH 140 may further add or remove fluid from each well 132 to perform additional concentration and/or elution of the genetic material, and may transfer fluid from the wells 132 of the sample microplate 130 to wells 152 of a genome stock microplate 150. The genome stock microplate 150 may be labeled with a unique identifier, and the contents of each well 152 of the genome stock microplate 150 may be associated with a corresponding LSI. In all phases of operation, the LH 140 is operated to ensure that fluid is not transferred between wells 152, as this results in contamination.

In one embodiment, a portion of fluid is removed from each well 152 of the genome stock microplate 150 for quality control purposes. Concentration of genetic material within the wells 152 may be confirmed via testing of this fluid, such as by application of a dye that reacts with the genetic material at known levels of fluorescence for known concentrations.

Library Preparation

After extraction is completed, library preparation may be performed for the contents of the genome stock microplate

150. The bead for each well, including ionically bonded genetic material, is transferred to a distinct well of a library preparation microplate (not shown). The library preparation microplate includes an identifier that uniquely distinguishes it from other library preparation microplates, and the LSI associated with each well on the genome stock microplate 150 may be mapped to a corresponding well on the library preparation microplate.

The library preparation microplate may be transferred to a new portion of the genomics laboratory 120 that is sealed from, and/or positively pressurized relative to, other portions of the genomics laboratory 120 that do not perform amplification of genetic material. This feature helps to prevent amplified genetic material from entering portions of the laboratory where genetic material has not been amplified, which could result in contamination. The transfer process may be performed by placing a library preparation microplate into an airlock at the pre-amplification portion of the genomics laboratory 120, sealing the airlock, and then retrieving the library preparation microplate from the airlock via the amplification portion of the genomics laboratory 120.

In one embodiment, a reagent is applied to each well of the library preparation microplate. The reagent ionically bonds to the surface of the bead within the well, and does so more strongly than the genetic material. This releases the genetic material from the surface of the bead of each well, enabling the genetic material to be chemically interacted with.

Library preparation may include normalization of a concentration of genetic material in each well of the library preparation microplate. Library preparation further includes fragmentation of the genetic material via an enzyme or via the application of physical forces. During this process, the entire genome (e.g., roughly three billion base pairs for a human genome), may be fragmented into pieces. In one embodiment, the pieces vary between three hundred and four hundred base pairs in length. These pieces are known as nucleic acid fragments.

In this embodiment, the nucleic acid fragments undergo adaptor ligation and indexing in accordance with known techniques. For example, this may comprise Next Generation Sequencing (NGS) library preparation processes defined by Illumina. Next, a limited amount of Polymerase Chain Reaction (PCR) amplification is performed upon the library. The resulting solution is then purified and eluted via operation of an LH 140.

During library preparation, one or more reference samples of genetic material, distinct from the genetic material found in the samples, may be added to wells of the library preparation microplate. The reference samples do not include genetic material received from a customer, but rather include known sequences of base pairs. The reference samples serve as controls to ensure that processes are carried out with sufficient quality.

Upon completion of library preparation, desired fragments of the genetic material (e.g., thousands or millions of distinct fragments of the genetic material, each corresponding with a different portion of a genome of the subject) have been ligated to predefined adapters (e.g., DNA adapters) that bind with the genetic material. Each of the adaptor-ligated fragments is referred to as a "library."

In further embodiments, the probes applied to each well of the library preparation plate include chemical identifiers (colloquially referred to as "barcodes") that are distinct from each other. The use of a different chemical identifier for probes applied to each well of the library preparation microplate enables sequencing to later be performed for multiple subjects on the same flow cell, without conflating sequencing results for those subjects.

The library preparation process may further comprise controlling a concentration of the genetic material in each well, and purification and/or elution of the resulting material. Similar to the processes performed after extraction of genetic material, concentration of genetic material after library preparation may be confirmed for each well via testing.

Enrichment

After library preparation, enrichment processes may be performed in order to either directly amplify (e.g., via amplicon or multiplexed PCR) or capture (e.g., via hybrid capture) predefined libraries. This enhances the ease of sequencing desired portions of the genome.

In one embodiment, during enrichment, customized biotinylated oligonucleotide probes are applied to the libraries. The probes selectively hybridize genetic material occupying desired portions of the genome for the genetic material, such as specific genes, or the entire exome. Magnetic beads bind to biotin molecules in the probes to attach the hybridized material to the magnetic beads. Magnetic forces capture the beads in place, enabling remaining fluid within each well to be removed or washed out, thereby removing impurities, and leaving only the genetic material that is desired. Genetic material may be released from the beads in a similar manner to that discussed above for prior processes.

In a further embodiment, hybrid capture target enrichment is performed. During this process, the probes comprise tailored oligonucleotides that are chosen to bind to the genetic material. The range of probes may be tailored as a group to bind to specific alleles, specific genes, the exome, the entire genome, etc. That is, each probe may bind to a nucleic acid fragment at a specific location on the genome, and the range of probes may be selected to ensure that alleles, genes, the exome, or the entire genome of the subject being considered is acquired. Utilizing probes in this manner may enhance efficiency of the sequencing process, by foregoing the need to sequence all of the roughly three billion base pairs found in the human genome.

The enrichment process may further comprise controlling a concentration of the genetic material in each well, and purification and/or elution of the resulting material. Similar to the processes performed after extraction of genetic material, concentration of genetic material after enrichment may be confirmed for each well via testing.

Sequencing

Sequencing may be performed according to any of a variety of techniques, including short-read and long-read techniques, via sequencing equipment 160 (e.g., an Illumina NovaSeq X sequencing machine). In one embodiment, the sequencing is performed as Sequencing by Synthesis (SBS). For example, sets of enriched libraries of genetic material bound to probes in earlier steps may be transferred to a flow cell, and annealed to oligonucleotide probes within the flow cell. At this stage, the contents of multiple wells may be applied to the same flow cell, because the libraries within those wells are tagged with the chemical identifiers referred to above. In one embodiment, the chemical identifiers comprise nucleotide sequences that are detectable during the sequencing process to determine a corresponding LSI.

Complementary sequences may then be created via enzymatic extension to create a double-stranded portion of genetic material. The double-stranded genetic material may then be denatured, and the library fragment may be washed away. Bridge amplification may then be performed to create copies of the remaining molecule in a localized cluster. For example, a cluster may comprise twenty to fifty copies of the same molecule, localized to a location the size smaller than a pinhead on the flow cell.

In this embodiment, sequencing primers are annealed to library adapters in order to prepare the flow cell for SBS. During SBS, the sequencing primer uses reverse terminator fluorescent oligonucleotides, one base per cycle, for a number of cycles (e.g., one hundred and fifty cycles) in the forward direction. After the addition of each nucleotide, clusters are excited by a light source, resulting in fluorescence which can be measured. The emission wavelength and signal intensity for each cluster determines a base call for that cluster. Fluorescent moieties are then flushed from the flow cell. A chemical group blocking a 3' end of the fragment is then removed, enabling a subsequent nucleotide to be read. This tightly controls nucleotide addition and detection.

Additionally in this embodiment, base calls across cycles at the same physical location on the flow cell occur at the same cluster, and hence indicate sequential reads for copies of the same fragment of the genetic material. After each cycle, denaturing and annealing are performed to extend the index primer. A complementary reverse strand is created and extended via bridge amplification. The reverse strand is then read in the reverse direction for a number of cycles, in a manner similar to reads in the forward direction.

Depending on whether a complete human genome, or another set of genomic data, is being tested, different reagents (e.g., probes, primers, etc.) may be chosen. That is, different reagents may be utilized for library preparation for a pathogen (e.g., bacteria, virus) or an organelle (e.g., mitochondria) than for a human genome. Pathogens exhibiting Ribonucleic Acid (RNA) genomes may have their genetic material translated to DNA before sequencing, enrichment, and/or library preparation are performed, via known techniques, such as Next Generation Sequencing (NGS) techniques.

Throughout the processes discussed above, the laboratory environment may be carefully controlled to ensure quality. For example, temperature within each segment of the laboratory may be carefully monitored and controlled, and ultraviolet lighting or other features capable of inactivating genetic material may be carefully positioned to ensure that contamination does not occur.

Bioinformatics

Sequencing data may be stored in any suitable format. In one embodiment, raw sequencing data generated during synthesis is stored in a file format such as Binary Base Call (BCL). This raw data may be fed to an analytical pipeline such as a cloud-based computing environment. Raw sequencing data may be processed by the pipeline into a second format, such as a text-based FASTQ format, that reports quality scores. The second format may then be analyzed to perform alignment of sequence reads to a reference genome, such as a reference genome reported in a Browser Extensible Data (BED) file. The aligned sequence data may be reported as a Binary Alignment Map (BAM) file or Compressed Reference-oriented Alignment Map (CRAM) file. The aligned sequence data may then be called, resulting in a Variant Call Format (VCF) file reporting called variants at each location of the genome that was sequenced, together with secondary metrics such as quality indicator metrics. As used herein, a variant comprises a unique combination of genetic information, in the form of consecutive base pairs at a specific set of locations (e.g., genomic coordinates) along a portion of a chromosome. Each variant is distinguished from other variants by having a different combination of base pairs along the set of locations. This may be due to Single Nucleotide Polymorphisms (SNPs) which relate to common single nucleotide changes, Single Nucleotide Variants (SNVs) which relate to rare nucleotide changes, insertions and/or deletions (Indels) which relate for example to the insertion or deletion of less than thirty base pairs, or differing numbers of repetitions, Copy Number Variants (CNVs), which relate to larger insertions or deletions, translocations, inversions, other types of genetic variants, or even combinations of variants, such as haplotypes or Multi-nucleotide variants (MNVs).

The called sequence data may be provided to a data analyst via a User Interface (UI), such as a Graphical User Interface (GUI) presented via a display. An example of such is illustrated in FIG. 4. The technician may then validate the resulting variants called from the sequence data and release it for reporting to subjects, healthcare providers, and/or scientists.

Genomics Architecture

Figure 2:
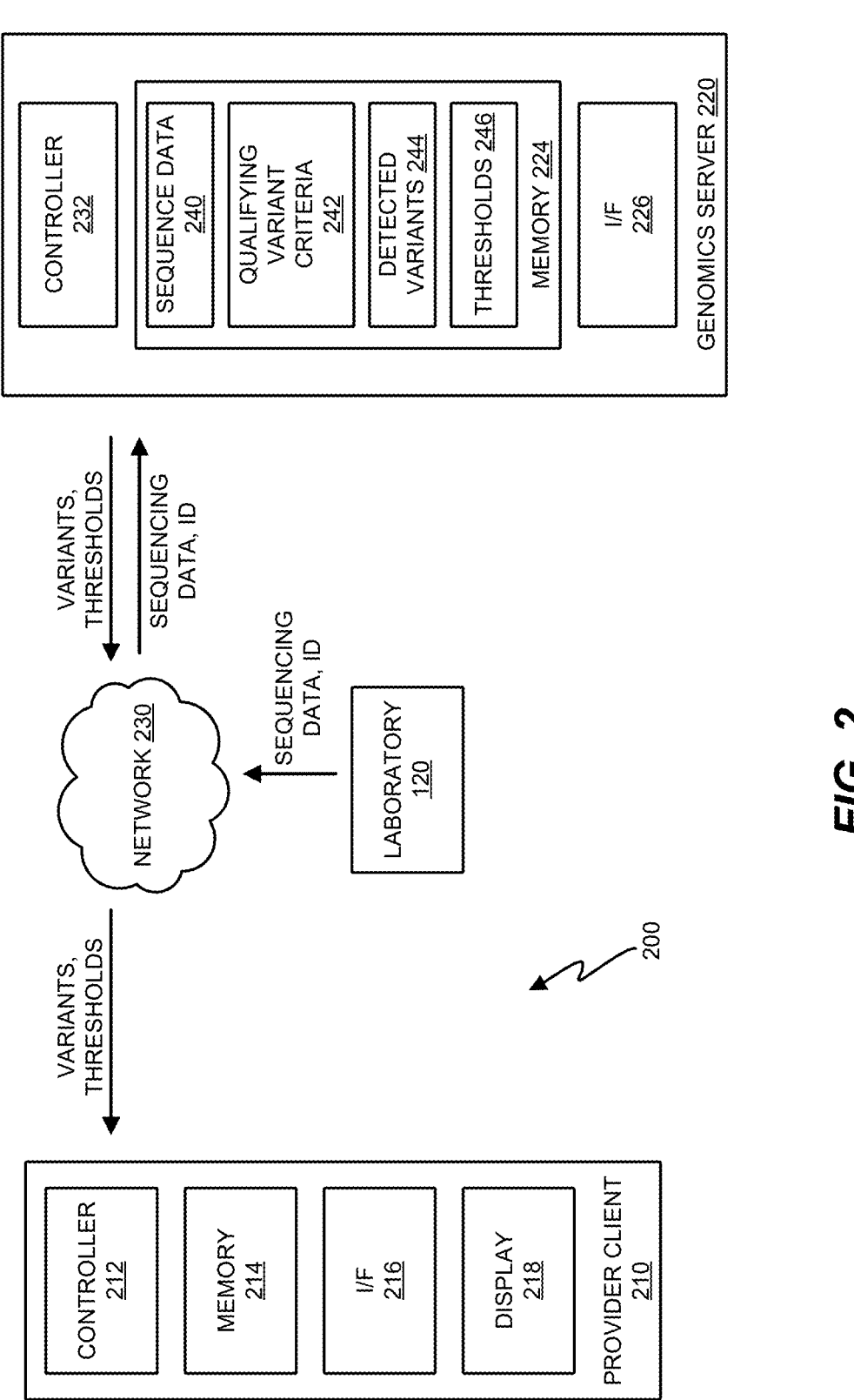
FIG. 2 is a block diagram illustrating a genomics architecture, in an illustrative embodiment.

FIG. 2 is a block diagram illustrating a genomics architecture 200 in an illustrative embodiment. Genomics architecture 200 comprises any combination of systems and devices operable to review, process, and/or control access to sequencing data, including sequencing data received from genomics laboratory 120. In this embodiment, genomics architecture 200 comprises a genomics server 220 which receives sequencing data and identifiers (e.g., CSIs 108, LSIs, etc.) from genomics laboratory 120, via network 230.

Genomics server 220 receives the sequencing data via interface (I/F) 226, such as an Ethernet interface, wireless interface compliant with Institute of Electrical and Electronics Engineers (IEEE) 802.11 standards, or other physical interface capable of transmitting and receiving digital data. The sequencing data 240 is stored in memory 224 for the population of patients (e.g., millions of patients) that have been sequenced by laboratory 120, and may be maintained in any suitable format. Examples of such formats include CRAM, VCF, BAM, and others. Memory 224 may store, for example, sequence data 240 describing multiple patients, and this sequence data 240 may be maintained in a de-identified format to facilitate the advancement of research. Memory 224 may be implemented via a cloud storage service, or may comprise a storage medium such as a hard disk or flash memory device.

Memory 224 additionally stores qualifying variant criteria 242, detected variants 244, and thresholds 246 for diagnosis and/or treatment of various conditions associated with the variance 244. Examples include Centers for Disease Control (CDC) Tier 1 conditions, cardiomyopathy, pharmacogenomics sensitivities, BRCA1 and BRCA2 gene variants associated with breast cancer, GCK variants associated with type 2 diabetes, etc. In one embodiment, the portion of memory 224 storing these components is distinct from the portion of memory 224 storing sequence data 240.

Controller 232 manages the operations of genomics server 220, and may for example analyze sequence data 240 to identify detected variants 244, control access and authentication related to sequence data 240, communicate with one or more provider clients 210, and/or perform additional operations. Controller 232 may be implemented, for example, as custom circuitry, as a hardware processor executing programmed instructions, as a combination of shared hardware processing resources implementing a compute service, or some combination thereof.

Genomics architecture 200 further comprises provider client 210, which is configured to receive information regarding detected variants 244 and/or thresholds 246. In this embodiment, provider client 210 includes a controller 212, a memory 214, an interface (I/F) 216, and a display 218. Controller 212 manages the operations of the provider client 210, and may be implemented, for example, as custom circuitry, as a hardware processor executing programmed instructions, or some combination thereof. Memory 214 comprises information for interpreting the data received via I/F 216. Display 218 may comprise a projector, screen, etc. for presenting information to a user of provider client 210.

Interpreting Sequencing Data

After sequencing data for the patient has been acquired (e.g., as an accompaniment to blood testing, in a prior event that provided a sample 106, etc.), sequencing data for the genes is reviewed for that patient by controller 232 of genomics server 220. For example, the sequencing data may be reviewed across the entire genome or exome, including for one or more genes that contribute to a specific phenotype or disease.

Figure 3:
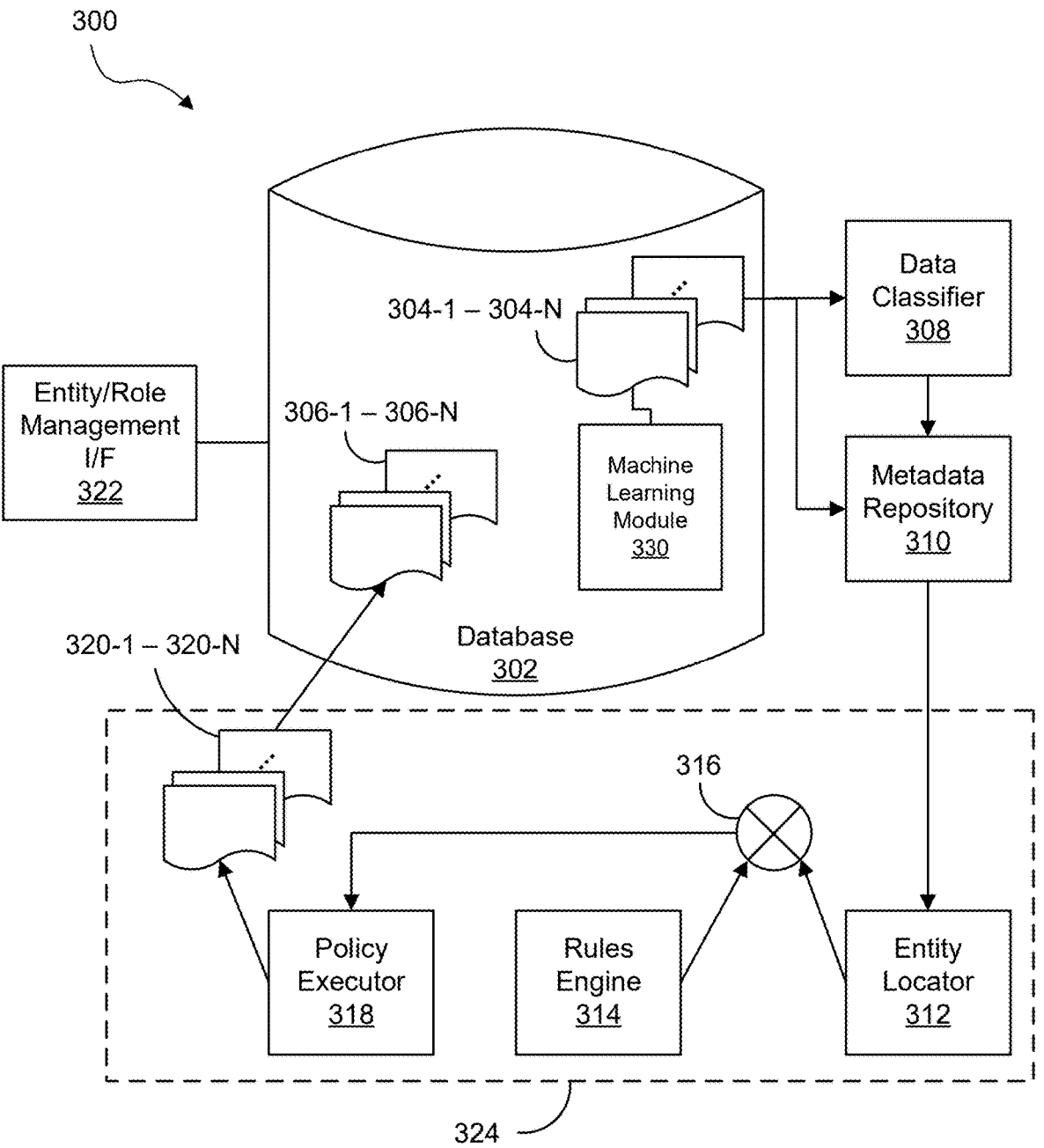
FIG. 3 is a block diagram of a system for controlling access to all or portions of electronic patient records, in an illustrative embodiment.

With the foregoing description provided of illustrative systems for sample intake and sequencing, the following FIGS. 3-6 describe illustrative techniques for dynamic identification and access control for sensitive data including such sample intake and processing. For example, FIG. 3 is a block diagram of a sample processing architecture 100 for controlling access to all or portions of electronic patient records 304-1-304-N (where the reference "N" is an integer greater than "1", and not necessarily equal to any other "N" reference designated herein), in an illustrative embodiment.

In this embodiment, the system 300 is configured with a database 302 that is operable to store electronic patient records 304 as well as a plurality of rules 306-1-306-N governing access to various elements in each of the electronic health records 304. For example, the electronic patient records 304 may be configured as data structures within the database 302 with each data structure comprising a plurality of data elements that may include PII (e.g., patient names, phone numbers, addresses, etc.), PHI (e.g., patient prescription information, gene sequencing data of patients, healthcare provider notes, disease information, etc.). An example of such is shown and described in FIGS. 4A and 4B.

The rules 306 control how entities (e.g., healthcare providers, individual users, clinical diagnostic organizations, administrative professionals, accounting professionals, etc.) view and access individual data elements within the data structures. For example, if an entity with limited access logs into the system 300, the system 300 identifies the entity and the entity's access level and selects an appropriate rule 306 to implement. The selected rule may allow the entity to retrieve and view only a limited amount of data, such as publicly available data. Generally, the rules 306 may control access based on an access to public data, access to confidential data, access to data having indirect identifiers for PII and/or PHI, access to data having direct identifiers for PII and/or PHI, access to genetic data, access to restricted data, and the like. Examples of direct identifiers for PII and/or PHI include names, Social Security numbers, etc. Examples of indirect identifiers for PII and/or PHI include phone numbers, addresses, and any other information that may be used to deduce a particular patient in the electronic patient records 304. Examples of restricted data may include healthcare diagnoses, prescription information, etc.

During initialization (and periodically afterwards, such as daily), a data classifier 308 reviews the database 302 to automatically classify data within the database 302. The data classifier 308 may operate using a combination of training data and input parameters to assign classifications to the electronic patient records 304 on a data element by data element basis so as to tag the presence of PII, PHI, and/or other information.

The data classifier 308 may operate to classify and tag the data elements in the electronic patient records 304 in a variety of ways. For example, the data classifier 308 may be provided with specific expressions to observe in data that is expression based (e.g., in a regular and predetermined form). For other kinds of data where there is no specific pattern, the data classifier 308 may employ a machine learning process, such as a Large Language Model (LLM) to review the data and apply tags. This model generally takes into account context within the data elements being considered. For example, if there is a date column next to a name column, the date may be tagged as date of birth.

The data classifier 308, upon classifying and tagging the data elements of the electronic patient records 304, reports this information to a controller 324 that manages interactions with the database by various entities. The controller 324 retrieves metadata from a metadata repository 310. The metadata repository 310 stores information that indicates which entity roles are granted access to various classifications of data in the data elements of the electronic patient records 304. Based on this information, the controller 324 generates stored procedures (e.g., prepared SQL code) for each electronic patient record 304 and each entity role.

For example, an entity locator 312 may identify all entities with access to the electronic patient records 304. The entity locator 312 may retrieve metadata associated with each of those entities to determine a level of access to the electronic patient records 304 of the database 302. A rules engine 314, having access to the rules 306, supplies the rules 306 to a rules/entity reconciliation module 316, which applies the rules 306 to each entity based on the determined level of access to the electronic patient records 304. The rules reconciliation module 316 then generates a policy for each entity dictating how each entity can access various data elements of the electronic patient records 304. That is, the policy may: dictate whether an entity can view all or certain data elements of the electronic patient records 304; dictate whether all or certain data elements of the electronic patient records 304 are masked, encrypted, nulled, etc.; or the like.

From there, a policy executor 318 applies those policies to the entities having access to the database 302 to generate a policy data structure for each entity (i.e., policy data structures 320-1-320-N). The policy data structures 320 may then be conveyed to the database 302 such that, when a particular entity logs into the database 302 to retrieve one or more electronic patient records 304, the entity/role management interface 322 will verify the entity's access level to the electronic patient records 304.

To illustrate, the controller 324, for every rule r in a set of rules R (e.g., rules 306), identifies a set of labels L that are defined for a rule r. The rule r applies to all entities in the system 300 that are marked with labels in the set L. Then, for every label l in the set of labels L:

via the entity locator 312, identify the set of entities E that have attributes labeled l, the labeling being performed by the data classifier 308 and stored in the metadata repository 310;

for every attribute attr labeled with l:

via the rules engine 314, generate a masking policy, if necessary, based on the rule r, including information about a datatype of the attribute attr;

perform a masking function for the data elements of the electronic patient record(s) 304 defined by a masking policy for the rule r (e.g., redacting information, format preserving masking, and/or hashing or null-
ing values of data elements);
attach the masking policy to the attribute attr (i.e., the
default masking policy for this attribute attr);
via a policy executor 318, generate a policy, if neces-
sary, that allows data to be seen by entities assigned
to roles that are allowed to see (i.e., an identity
function); and
via the policy executor 318, assign the policy to all the
roles that are allowed to see the data unmasked.

One example of a policy generation may incorporate the
following pseudocode:
Mask columns tagged "Sensitive" using a constant
"REDACTED" for everyone except for users in role
"Data Classification 1" or "Data Classification 2".

One example of a rule generation may incorporate the
following pseudocode:
Create MASKING POLICY SHOW_samples_table if it
does not exist with (first_name varchar(21)) using
(first_name); and
Create MASKING POLICY HIDE_samples_table if it
does not exist with (first_name varchar(21)) using
('REDACTED'::TEXT).

The rules may then be attached to roles and/or groups as
follows:
The SHOW_samples_table policy may be attached to
these two roles/groups "Data Classification 1" or "Data
Classification 2" for the column first_name by:
attaching MASKING POLICY HIDE_samples_table on
samples(first_name) to "Data Classification 1"; and
attaching MASKING POLICY HIDE_samples_table on
samples(first_name) to "Data Classification 2".
The HIDE_samples_table policy may be attached by
default to public entities for the column first_name by:
attaching MASKING POLICY HIDE_samples_table on
samples(first_name) to PUBLIC priority 0.

After initialization, the system 300 transitions to an opera-
tional phase where entities can provide queries to the
electronic patient records 304 of the entity/role management
interface 322. Each query may be accompanied by metadata
indicating an entity role for the entity that has logged into the
system 300 through the entity/role management interface
322 to query the database 302. As each query is received for
one or more electronic patient records 304, the controller
324 reviews stored procedures for the electronic patient
record(s) 304 for that entity's role, and dynamically pro-
vides the data of the data elements, redacts certain data
elements, masks certain data elements, sets certain data
elements to null, and/or hash encrypts certain data elements
based on the entity role. The controller 324 then directs the
database 302 to provide the electronic patient record(s) 304
in real-time by immediate detection and application of the
corresponding policy.

In other words, the entity/role management interface 322
may then select one or more of the rules 306 based on a
given policy data structure 320 for the entity to apply to the
data elements of the electronic patient records 304 being
retrieved by the entity. The database 302 may then allow the
entity to view all of the information in the data elements of
the electronic patient records 304, mask a portion of the
information in the data elements of the electronic patient
records 304, encrypt a portion of the information in the data
elements of the electronic patient records 304, null a portion
of the information in the data elements of the electronic
health records 304, etc. And entity roles may be provided in
escalating levels of access, such as a higher-level entity role for accessing all classifications of data accessible to a
lower-level entity role, in addition to one or more further
classifications of data.

In some embodiments, the system 300 is capable of
detecting the addition of new data elements in any given
electronic patient record 304, and/or entire electronic patient
records 304 themselves. In this regard, the database 302 may
include a machine learning module 330 that may learn from
the electronic patient records 304 within the database 302 so
as to identify the new data elements and their significance to
the electronic patient records 304 (e.g., by classifying and
tagging the new data elements as discussed above). Until the
new data elements are learned, the system 300 may restrict
access to all entities to prevent the divulgation of the
information to any unauthorized personnel. Once learned,
the data classifier 308 may tag the new data elements such
that new policies can be generated on an entity by entity
basis.

FIG. 4A illustrates various electronic patient records 304,
in an illustrative embodiment. In this embodiment, a plu-
rality of electronic patient records 400 are illustrated with
various data elements including a customer name 402A, a
market segment that the customer operates in 404, a phone
number of the customer 406A, an account balance of the
customer 408A, and a general income level of the customer
410A. The electronic patient records 400 may include other
information of a customer (e.g., a patient) as well, such as
prescriptions, gene sequencing data, medical diagnoses, etc.
For the purpose of this example, however, the data elements
of the electronic patient records 400 may be desired by
accounting personnel of a healthcare provider. And, as such,
medical history information, healthcare provider informa-
tion, etc. would not be required by accounting personnel.
Accordingly, this information would be blocked from view
from accounting personnel.

FIG. 4B illustrates the electronic patient records of FIG.
4A with various forms of access control being implemented,
in an illustrative embodiment. Now, with respect to the
embodiment of FIG. 4A, assume that the accounting per-
sonnel is an admin person requesting information pertaining
to overall account balances of patients of a healthcare
provider to perform accounting analysis for the healthcare
provider. In this regard, the admin person may not require
access to customer names 402, their market segments 404,
or their phone numbers 406. Based on the policy for this
admin person, the customer names 402B of the electronic
patient records 400 may be masked with the values
"XXXXXXXX" and their market segments 404B may be
nulled out. Additionally, the phone numbers 406B, as they
are unnecessary to the admin person seeking to perform
routine accounting analysis for the healthcare provider, may
be hash encrypted so as to prevent an indirect reveal of the
customers' PII. However, as the admin person may require
access to account balances and income levels for general
accounting analysis of the healthcare provider, the admin
person may be permitted access to those data elements in the
electronic patient records 400. Accordingly, the account
balance 408B and income level 410B may be revealed to the
admin person when that person logs in to the system 300
described herein.

In some embodiments, hash encryption, such as that
performed for the phone numbers 406B, may be accom-
plished using any suitable hashing function including a
one-to-one hashing function. In some embodiments, values
may be subjected to a combination of format-preserving
masking and hashing. For example, a phone number may be
presented as "(bcc)-6f8-ae27" instead of "(XXX)-XXX- XXXX" to preserve the phone number format. Each operation may have different use cases. For example, using a one-to-one hashing function on certain data elements, and providing a hashed version of the data, may result in unique entries being detectable within the hashed data, because they have a unique corresponding hash. This permits an entity to count unique and non-unique values within a column if necessary.

FIG. 5 is a flowchart of a process 500 providing access control to electronic patient records, such as those shown and described above, in an illustrative embodiment. In this embodiment, an entity may log into the system 300 of FIG. 3 to request access to one or more of a plurality of electronic patient records 304. As the process 500 generally regards an operational phase of the system 300, the electronic patient records 304 have already been machine learned to identify patient information in the electronic patient records, including PII and PHI. Thus, the system 300 may receive and process the request, in the process element 502, and then determine a level of access of the entity making the request, in the process element 504. Such may also include identifying a user role for the entity when the entity logs into the system 300.

The system 300 may retrieve the one or more electronic patient records 304 requested by the entity, in the process element 506. Thus, upon the determination of the entity's level of access, the system 300 may apply a rule to the retrieved electronic patient records to mask, encrypt, null, and/or show various data elements within the retrieved electronic patient records, in the process element 508. Generally, masking involves the replacement of all or a portion of data in a field with new values. Encryption generally involves transforming data according to a predefined function in a manner that cannot be reversed without a key or a password. And nulling generally involves replacing data within a field with a NULL value. Once this operation is complete, the system 300 may transfer the requested electronic patient records 304 to the entity, in the process element 510.

While the exemplary embodiments herein are shown and described with respect to electronic patient records, these embodiments are not intended to be limited to such. Rather, the embodiments herein may be expanded to identify and tag data elements in any of a variety of data structures based on a level of access to the data elements.

The embodiments herein provide notable improvements over prior techniques of data access control because they essentially eliminate multiple sources of human error, while also vastly expanding the volume of data tables that may be considered/reviewed for sharing. Furthermore, the embodiments herein may be performed on a live operating database, even as that database is being accessed, updated, and/or altered.

Any of the various computing and/or control elements shown in the figures or described herein may be implemented as hardware, as a processor implementing software or firmware, or some combination of these. For example, an element may be implemented as dedicated hardware. Dedicated hardware elements may be referred to as "processors," "controllers," or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

In one embodiment, instructions stored on a computer readable medium direct a computing system of any of the devices and/or servers discussed herein, such as genomics server 220, to perform the various operations disclosed herein. In some embodiments, all or portions of these operations may be implemented in a networked computing environment, such as a cloud computing system. Cloud computing often includes on-demand availability of computer system resources, such as data storage (cloud storage) and computing power, without direct active management by an entity. Cloud computing relies on the sharing of resources, and generally includes on-demand self-service, broad network access, resource pooling, rapid elasticity, and measured service.

Figure 6:
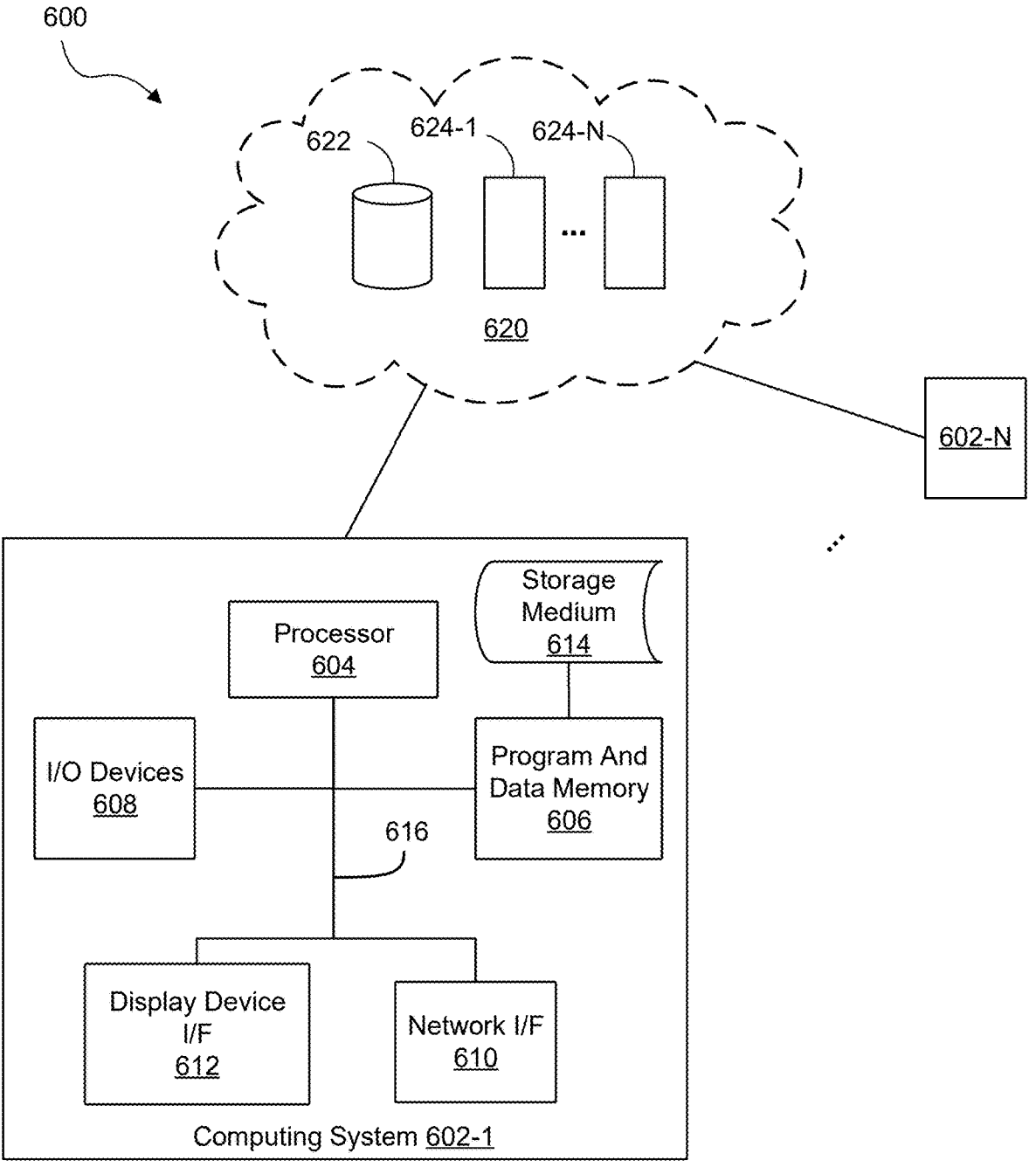
FIG. 6 depicts an illustrative cloud computing system operable to execute programmed instructions embodied on a computer readable medium.

FIG. 6 depicts one illustrative cloud computing system 600 operable to perform the above operations by executing programmed instructions tangibly embodied on one or more computer readable storage mediums. The cloud computing system 600 generally includes the use of a network of remote servers hosted on the internet to store, manage, and process data, rather than a local server or a personal computer (e.g., in the computing systems 602-1-602-N). Cloud computing enables users to use infrastructure and applications via the internet, without installing and maintaining them on-premises. In this regard, the cloud computing network 620 may include virtualized information technology (IT) infrastructure (e.g., servers 624-1-624-N, the data storage module 622, operating system software, networking, and other infrastructure) that is abstracted so that the infrastructure can be pooled and/or divided irrespective of physical hardware boundaries. In some embodiments, the cloud computing network 620 can provide users with services in the form of building blocks that can be used to create and deploy various types of applications in the cloud on a metered basis.

Various components of the cloud computing system 600 may be operable to implement the above operations in their entirety or contribute to the operations in part. For example, a computing system 602-1 may be used to perform analysis of gene sequencing data, and then store that analysis along with the gene sequencing data in a data storage module 622 (e.g., a database) of a cloud computing network 620. Various computer servers 624-1-624-N of the cloud computing network 620 may be used to operate on the gene sequencing data and/or transfer the gene sequencing analysis and/or the gene sequencing data to another computing system 602-N.

Some embodiments disclosed herein may utilize instructions (e.g., code/software) accessible via a computer-readable storage medium for use by various components in the cloud computing system 600 to implement all or parts of the various operations disclosed hereinabove. Examples of such components include the computing systems 602-1-602-N.

Exemplary components of the computing systems 602-1-602-N may include at least one processor 604, a computer readable storage medium 614, program and data memory 606, input/output (I/O) devices 608, a display device interface 612, and a network interface 610. For the purposes of this description, the computer readable storage medium 614 comprises any physical media that is capable of storing a program for use by the computing system 602. For example, the computer-readable storage medium 614 may be an electronic, magnetic, optical, electromagnetic, infrared, semiconductor device, or other non-transitory medium. Examples of the computer-readable storage medium 614 include a solid-state memory, a magnetic tape, a removable computer diskette, a random access memory (RAM), a read-only memory (ROM), a rigid magnetic disk, and an optical disk. Some examples of optical disks include Compact Disk-Read Only Memory (CD-ROM), Compact Disk-Read/Write (CD-R/W), Digital Versatile Disc (DVD), and Blu-Ray Disc.

The processor 604 is coupled to the program and data memory 606 through a system bus 616. The program and data memory 606 include local memory employed during actual execution of the program code, bulk storage, and/or cache memories that provide temporary storage of at least some program code and/or data in order to reduce the number of times the code and/or data are retrieved from bulk storage (e.g., a hard disk drive, a solid state drive, or the like) during execution.

Input/output or I/O devices 608 (including but not limited to keyboards, displays, touchscreens, microphones, pointing devices, etc.) may be coupled either directly or through intervening I/O controllers. Network adapter interfaces 610 may also be integrated with the system to enable the computing system 602 to become coupled to other computing systems or storage devices through intervening private or public networks. The network adapter interfaces 610 may be implemented as modems, cable modems, Small Computer System Interface (SCSI) devices, Fibre Channel devices, Ethernet cards, wireless adapters, etc. Display device interface 612 may be integrated with the system to interface to one or more display devices, such as screens for presentation of data generated by the processor 604.

What is claimed is:

1. A computer implemented method, comprising:
receiving a request from an entity for access to one or more of a plurality of electronic patient records, the plurality of electronic patient records having been machine learned to identify patient information in the electronic patient records including personally identifiable information (PII) and protected health information (PHI);
determining a level of access of the entity;
retrieving, from a database, the one or more electronic patient records requested by the entity;
applying a rule to the retrieved one or more electronic patient records based on the determined level of access of the entity to at least one of mask, encrypt, or show one or more elements in the one or more electronic patient records;
in response to applying the rule to the retrieved one or more electronic patient records, transferring the one or more electronic patient records to the entity;
receiving a new electronic patient record; and
machine learning the new electronic patient record with a machine learning model that has been trained on the plurality of electronic patient records.

2. The computer implemented method of claim 1, wherein:
encrypting the one or more elements in the one or more electronic patient records comprises applying a hash encryption to the one or more elements in the one or more electronic patient records.

3. The computer implemented method of claim 1, further comprising:

restricting access to all elements of the new electronic patient record until all elements of the new electronic patient record have been identified.

4. The computer implemented method of claim 1, further comprising:
receiving a new element to at least one of the plurality of electronic patient records; and
restricting access to the new element of the at least one electronic patient record until the new element of the at least one electronic patient record has been identified.

5. The computer implemented method of claim 1, wherein:
determining a level of access of the entity further comprises retrieving metadata from a repository, the metadata indicating the entity's role to access classifications of data in the elements of the one or more electronic patient records such that the rule may be selected and applied to the retrieved one or more electronic patient records.

6. The computer implemented method of claim 1, wherein:
the level of access of the entity includes one of access to public data, access to confidential data, access to data having indirect identifiers for PII and/or PHI, access to data having direct identifiers for PII and/or PHI, access to genetic data, and access to restricted data.

7. A non-transitory computer readable medium embodying programmed instructions which, when executed by a processor, are operable for performing a method for securing data in a plurality of electronic patient records, the method comprising:
receiving a request from an entity for access to one or more of the plurality of electronic patient records, the plurality of electronic patient records having been machine learned to identify patient information in the electronic patient records including personally identifiable information (PII) and protected health information (PHI);
determining a level of access of the entity;
retrieving, from a database, the one or more electronic patient records requested by the entity;
applying a rule to the retrieved one or more electronic patient records based on the determined level of access of the entity to at least one of mask, encrypt, or show one or more elements in the one or more electronic patient records;
in response to applying the rule to the retrieved one or more electronic patient records, transferring the one or more electronic patient records to the entity;
receiving a new electronic patient record; and
machine learning the new electronic patient record with a machine learning model that has been trained on the plurality of electronic patient records.

8. The non-transitory computer readable medium of claim 7, wherein:
encrypting the one or more elements in the one or more electronic patient records comprises applying a hash encryption to the one or more elements in the one or more electronic patient records.

9. The non-transitory computer readable medium of claim 7, further comprising instructions which, when executed by the processor, are operable for:
restricting access to all elements of the new electronic patient record until all elements of the new electronic patient record have been identified.

10. The non-transitory computer readable medium of claim 7, further comprising instructions which, when executed by the processor, are operable for:

receiving a new element to at least one of the plurality of electronic patient records; and restricting access to the new element of the at least one electronic patient record until the new element of the at least one electronic patient record has been identified.

11. The non-transitory computer readable medium of claim 7, wherein:

determining a level of access of the entity further comprises retrieving metadata from a repository, the metadata indicating the entity's role to access classifications of data in the elements of the one or more electronic patient records such that the rule may be selected and applied to the retrieved one or more electronic patient records.

12. The non-transitory computer readable medium of claim 7, wherein:

the level of access of the entity includes one of access to public data, access to confidential data, access to data having indirect identifiers for PII and/or PHI, access to data having direct identifiers for PII and/or PHI, access to genetic data, and access to restricted data.

13. A system, comprising:

a database operable to store a plurality of electronic patient records that have been machine learned to identify patient information in the electronic patient records including personally identifiable information (PII) and protected health information (PHI), and to store rules to at least one of mask, encrypt, or show one or more elements in the plurality of electronic patient records based on a determined level of access;

an interface operable to receive a request from an entity for access to one or more of the plurality of electronic patient records;

a processor; and a memory comprising instructions that direct the processor wherein the database is further operable to determine a level of access of the entity, to retrieve, from the database, the one or more electronic patient records requested by the entity, to apply at least one of the rules to the retrieved one or more electronic patient records based on the determined level of access of the entity, wherein, in response to applying the at least one rule to the retrieved one or more electronic patient records, the interface is further operable to transfer the one or more electronic patient records to the entity, wherein the database is further operable to receive a new electronic patient record, and wherein the system further comprises a machine learning model that has been trained on the plurality of electronic patient records, the machine learning model being operable to machine learn the new electronic patient record.

14. The system of claim 13, wherein:

the database is further operable to encrypt the one or more elements in the one or more electronic patient records by applying a hash encryption to the one or more elements in the one or more electronic patient records.

15. The system of claim 13, wherein:

the database further operable to restrict access to all elements of the new electronic patient record until all elements of the new electronic patient record have been identified.

16. The system of claim 13, wherein:

the database is further operable to receive a new element to at least one of the plurality of electronic patient records, and to restrict access to the new element of the at least one electronic patient record until the new element of the at least one electronic patient record has been identified.

17. The system of claim 13, wherein:

the database is further operable to retrieve metadata from a repository, the metadata indicating the entity's role to access classifications of data in the elements of the one or more electronic patient records such that the rule may be selected and applied to the retrieved one or more electronic patient records.

18. The system of claim 13, wherein:

the level of access of the entity includes one of access to public data, access to confidential data, access to data having indirect identifiers for PII and/or PHI, access to data having direct identifiers for PII and/or PHI, access to genetic data, and access to restricted data.

* * * * *